US012714814B2

(12) United States Patent
Ananthanarayanan et al.

(10) Patent No.: US 12,714,814 B2
(45) Date of Patent: Aug. 25, 2026

(54) SUPRAGLOTTIC AIRWAY DEVICE WITH A DYNAMIC CUFF WITH SUPERIOR VENTILATING CAPABILITY

(71) Applicants: Kalyanaraman Ananthanarayanan, Tamil Nadu (IN); Kotak Nirav, Maharashtra (IN); Patyal Ashish, New Delhi (IN)

(72) Inventors: Kalyanaraman Ananthanarayanan, Tamil Nadu (IN); Kotak Nirav, Maharashtra (IN); Patyal Ashish, New Delhi (IN)

( * ) Notice: Subject to any disclaimer, the term of this patent is extended or adjusted under 35 U.S.C. 154(b) by 1637 days.

(21) Appl. No.: 16/968,251

(22) PCT Filed: Apr. 4, 2018

(86) PCT No.: PCT/IN2018/050191
§ 371 (c)(1),
(2) Date: Aug. 7, 2020

(87) PCT Pub. No.: WO2019/155481
PCT Pub. Date: Aug. 15, 2019

(65) Prior Publication Data

US 2021/0030985 A1 Feb. 4, 2021

(30) Foreign Application Priority Data

Feb. 7, 2018 (IN) ............................ 201821004603

(51) Int. Cl.
*A61M 16/04* (2006.01)
*A61B 5/00* (2006.01)
(Continued)

(52) U.S. Cl.
CPC ....... *A61M 16/0452* (2014.02); *A61B 5/0836* (2013.01); *A61B 5/6847* (2013.01);
(Continued)

(58) Field of Classification Search
CPC .. A61M 16/00; A61M 16/0003; A61M 16/04; A61M 16/0402; A61M 16/0409;
(Continued)

(56) References Cited

U.S. PATENT DOCUMENTS 4,495,948 A * 1/1985 Shapiro ............... A61M 16/042 128/207.15
5,241,956 A * 9/1993 Brain ................ A61M 16/0415 128/207.14
(Continued)

FOREIGN PATENT DOCUMENTS

CN 104667396 A 6/2015
CN 105050481 A 11/2015
(Continued)

OTHER PUBLICATIONS

Foreign Communication from a Related Counterpart Application, Indian Examination Report dated Jul. 3, 2021, Indian Application No. 202047021174 filed on May 20, 2020.
(Continued)

*Primary Examiner* — Colin W Stuart
(74) *Attorney, Agent, or Firm* — Conley Rose, P.C.

(57) ABSTRACT

This invention is a device to be used with a system for supplying anaesthetic or respiratory gases into the airway of a human or an animal. This device is a supraglottic airway device, which includes a shaft with three tubes one for ventilation purpose and rest two for dynamic cuff inflation and other for suctioning purpose. The dynamic cuff is inflated by the gases supplied directly from the anaesthesia or ventilator circuit through a specialised adaptor via dynalumen. The "cuff inflation lumen" ("DynaLumen") will also be having a locking mechanism to enable its use like a conventional LMA; i.e., the cuff can be left continuously inflated both during positive pressure ventilation as well as
(Continued)

less during expiratory phase and during spontaneous respiration.

9 Claims, 5 Drawing Sheets

(51) Int. Cl.
*A61B 5/083* (2006.01)
*A61M 16/08* (2006.01)

(52) U.S. Cl.
CPC .... *A61M 16/0409* (2014.02); *A61M 16/0436* (2014.02); *A61M 16/0479* (2014.02); *A61M 16/0486* (2014.02); *A61M 16/0816* (2013.01); *A61M 16/085* (2014.02); *A61M 2202/0225* (2013.01); *A61M 2205/073* (2013.01); *A61M 2210/065* (2013.01)

(58) Field of Classification Search
CPC .......... A61M 16/0415; A61M 16/0434; A61M 16/0436; A61M 16/044; A61M 16/0445; A61M 16/045; A61M 16/0452; A61M 16/0463; A61M 16/0486; A61M 16/0479; A61M 16/0454; A61M 16/0456; A61M 16/0459; A61M 16/0816; A61M 2210/065; A61M 2210/0656; A61M 39/00; A61M 39/02; A61M 39/10; A61M 39/1011; A61M 39/105; A61M 2039/1072; A61M 2039/1077
See application file for complete search history.

(56) References Cited

U.S. PATENT DOCUMENTS 5,282,464 A * 2/1994 Brain ................. A61B 5/14552 128/204.22
5,743,258 A * 4/1998 Sato ................. A61M 16/0484 128/207.14
5,983,897 A * 11/1999 Pagan ................... A61M 16/04 128/207.14
5,988,167 A * 11/1999 Kamen ............. A61M 16/0436 128/207.14
6,116,243 A * 9/2000 Pagan ............... A61M 16/0409 128/207.14
6,631,720 B1 * 10/2003 Brain .................... A61M 16/04 128/207.14
9,463,296 B2 10/2016 Stix
2008/0223374 A1 * 9/2008 Gonzaga Granja Filho ................ A61M 16/0875 128/207.15
2008/0308109 A1 * 12/2008 Brain ................ A61M 16/0816 128/207.14
2010/0300450 A1 12/2010 Barodka
2011/0220117 A1 9/2011 Dubach
2014/0000624 A1 1/2014 Miller
2016/0206841 A1 * 7/2016 Vadivelu ................. A61M 1/00
2016/0220773 A1 8/2016 Chang et al.
2016/0296719 A1 * 10/2016 Geraghty ............ A61M 16/085
2017/0065782 A1 * 3/2017 Acha Gandarias .......................... A61M 16/0409
2019/0038860 A1 * 2/2019 Lykins .................. A61M 16/04

FOREIGN PATENT DOCUMENTS

CN 106029145 A 10/2016
EP 0389272 A2 9/1990
EP 2965687 A1 1/2016
GB 2229367 A 9/1990
WO 0061213 A1 10/2000
WO 2015078204 A1 6/2015
WO 2015128207 A1 9/2015
WO 2016188536 A1 12/2016

OTHER PUBLICATIONS

Foreign Communication from a Related Counterpart Application, Indian Hearing Notice dated Jan. 4, 2024, Indian Application No. 202047021174 filed on May 20, 2020.

* cited by examiner 7
5
4
8
6a
2
6
4
9
10
1
12
11
3

4
6
10
17
18
13 compartment B
14 compartment A
15
16

7
5
6a
4a
8

4
6
10

Dynacuff lumen
Compartment B
Compartment A

SUPRAGLOTTIC AIRWAY DEVICE WITH A DYNAMIC CUFF WITH SUPERIOR VENTILATING CAPABILITY

FIELD OF INVENTION

The invention relates to a modified supraglottic airway device (SAD) with a dynamic cuff which will provide early and better airtight Supraglottic seal enabling superior ventilating ability. This device will help during general anaesthesia and during cardiopulmonary resuscitation in sick patients who require ventilatory support.

BACKGROUND AND PRIOR ART OF INVENTION

Traditionally general anaesthesia for surgical procedures was provided using "Endotracheal tubes" (aka 'Tracheal tubes'), which were cylindrical tubes inserted from the patients' mouth/nose into the patient's trachea via the patients' vocal cords.

This was done as the patients under general anaesthesia will not be able protect their "airways" (vocal cords, trachea, bronchi and lungs) resulting in increased risk of "aspiration pneumonitis", a life threatening condition. In addition to this, they will not be breathing sufficiently to maintain "Oxygenation" (meeting the Oxygen requirements of the body) and "Ventilation" (removal of Carbon dioxide from the body), the inability to do either of which can result in "Cardio respiratory arrest" (Death) within few to several minutes.

Tracheal tube were more invasive because the anaesthesiologist had to introduce a cylindrical tube through the vocal cords of the patient into the trachea. This was very painful and invasive, and it required high depth of anaesthesia to make the patient tolerate the placement of the endotracheal tube.

The patient will have to be maintained on Deep anaesthesia often more than what it required for simple surgeries, often exposing the patient to more anaesthetic agents than required by the surgery, making him vulnerable to the toxic side effects of the anaesthetic agents, including but not restricted to hemodynamic instabilities.

Due to these inherent disadvantages of the Endo tracheal tubes, a new category of airway devices by name of "Supraglottic airway devices" ("Glottis": Latin for Vocal Cords and the slit like opening between them which enables phonation and voice modulation) came into existence which were essentially devices which rest over the vocal cords (without entering the trachea and hence less uncomfortable for the patient undergoing surgery, and hence require a lighter anaesthetic plane to tolerate the same) and achieve the purpose of maintaining Oxygenation, Ventilation and with some protection against aspiration pneumonitis.

These devices have an inflatable "cuff" which rests in the "pharynx" of the patient, resting directly over the vocal cords, rather than extending all the way into the trachea as was the case with the endotracheal tubes.

These devices have a cylindrical, non kinkable "shaft" usually made of silicone or similar suitable material, with a proximal end and a distal end. The ventilator circuit/AMBU resuscitator is connected to the proximal end ("ventilator end") using a "universal connector" made of plastic or other suitable material. The shaft may have a bend/curve to conform to the normal anatomy of the upper airway.

There is a "lumen" inside the shaft which extends from the proximal end till the distal end. The distal end opens in a "bowl" directly over the glottis.

Surrounding the "bowl", at the distal end, lies a inflatable, oval shaped "cuff" which is inflated from the proximal end using a dedicated thin tube. The cuff, when inflated, fills up the pharyngeal space and exerts pressure along the pharyngeal wall in all directions, thereby creating an airtight seal on the glottis and the lower airway (Trachea, bronchi and lungs). The cuff will be able to maintain the airway seal as long as the "luminal pressure" is less than the "sealing pressure" (which is generally the intra-cuff pressure, which is exerted on the pharyngeal walls.

The Laryngeal Mask Airway (LMA) is the prototype of Supraglottic Airway Devices (SAD). As they require much lighter depth of anaesthesia (thereby reducing anaesthetic requirements) to be tolerated by the patient these devices are placed over the vocal cords enabling the patient to be ventilated mechanically if required (when the patient is in deeper planes of anaesthesia) and also enabling the patient to breath spontaneously (when the patient is in lighter planes of anaesthesia and also during awakening from anaesthesia).

These devices also prevent at the falling backward of the tongue in the unconscious patient ("tongue fall") and hence airway obstruction is also prevented, and the risk of aspiration pneumonitis is also minimal.

But the main problem with these devices is that the cuff has to be inflated to pressures of more than 30 cm of H20 to provide satisfactory seal for positive pressure ventilation. Whenever the luminal pressure exceeds cuff pressure, the device will not able to provide adequate seal, resulting in leakage of anaesthetic gases and Oxygen.

In patients with reactive Airways or the patients of bronchial asthma, the lower airway pressures, and hence the luminal pressure in the LMA, reaches to 40 cm of H20 which are higher. The Laryngeal Mask Airway devices can provide an effective Airways seal of only up to 25 centimetres of water, which may not be sufficient to provide satisfactory seal and ventilation.

In recent years certain new Supraglottic Airway Devices by name "Baska Mask" and "Air Q" been available in the market, employing self-pressurizing Supraglottic Cuff, i.e., the supraglottic "cuff" will be internally communicating with the "lumen" so that whenever the positive pressure ventilation is performed, the pressure will be transmitted from the lumen into the cuff, so that the patients lung and the supraglottic cuff both get inflated at the same time. This is a welcome design because in the traditional Laryngeal Mask Airways (LMA)/Supreglottic Airway Devices (SAD) the cuff stays inflated continuously. This can result in certain mechanical complications due to the cuff exerting continuous pressure on the pharyngeal structures, like sore throat, hoarseness of voice, and nerve injuries if the cuff stays inflated beyond a few hours. With these new type of devices where the cuff pressure closely mimics the luminal pressure, the cuff deflates during exhalation and hence there is no continuous pressure on the lingual nerve or the hypoglossal nerve like in the older designs. So these devices were safer with relation to the abovementioned complications due to "mechanical compression". But these devices had functional limitations. There are clinical studies which have proven that their cuff is not effective to provide air tight seal if the Airway ('Luminal') pressure exceeds 30 cm of H20.

So the need of the hour is a device which can have a self pressurizing cuff, in which the cuff can get inflated slightly earlier than the lung and maintain supraluminal cuff pressure throughout the inspiration (Positive pressure ventilation)

and deflate immediately after the positive pressure ventilation (expiratory phase of the respiratory cycle) gets over so that the cuff doesn't exert any undue continuous pressure on the pharyngeal structures. The device should also be capable of maintaining adequate supraglottic seal even if the luminal/Airway pressure exceeds 35-40 cm of H20.

Disadvantages of the Existing Device:

The existing devices which are available in the market for similar usage are the Laryngeal Mask Airway (LMA) and its variants, and other supraglottic Airway devices like Igel, proseal LMA, Air Q, and BaskaMask.

The Laryngeal Mask Airway (LMA) is having an inflatable cuff around supraglottic 'bowl', a long stem with a lumen connecting the proximal end to the distan end, which ends in the bowl, and an universal connector which connects the lumen of the proximal end to the ventilating circuit/AMBU bag. The inflatable cuff is attached to a distal tip of a narrow tube and it can be inflated from its proximal end after the bowl is securely placed in the pharynx. The main disadvantage of the laryngeal Mask Airway is that the cuff is inflated with cuff pressure of approximately 25 to 30 centimetre of water so there is a chance that there may be a leak during positive pressure ventilation resulting in exposing the patient to risk of aspiration. Also continuous inflated cuff can damage the cricopharyngeal nerve, lingual nerve and the hypoglossal nerve when kept inflated for more than few hours and can lead to post operative hoarseness of voice and Neuralgia, Igel SS supraglottic device is not having inflatable cuff so it safeguards the patient from the other LMA like inflation of the cuff leading to nerve injuries here the main problem will be the sealing pressure which will be considerably less than the positive pressure ventilation and may not be effective beyond peak pressure of 25 cm of H20.

Proseal LMA is having a slightly better seal but still it too employs an inflatable cuff which will have to be inflated for prolonged periods for effective positive pressure ventilation this also will have similar leak if the cuff pressure is less than 25 cm of H20 and prolonged use can cause nerve injuries.

AirQ is a recent supraglottic device which employs their self pressurizing cuff which inflates during positive pressure ventilation and deflates during exhalation. The main advantage of this device is that since the cuff doesn't stay inflated continuously, the chance of nerve injury is very minimal but the disadvantage of this device is that since the cuff pressure is almost equal to the luminal pressure and the cuff starts to inflate only during the time when the Airway pressure increases, there is inadequate seal of the airway if the luminal pressure exceeds 30 cm of H20.

The Baska Mask where the seal is better up to 40 cm of H20 of luminal pressure but Baska Mask is a slightly complicated device to manufacture and it is only a single use device impossible for it to be reused. Moreover in the Baska Mask the self pressurizing cuff get inflated only upon air entering the pharynx, that is when inspiration starts so there will be a time lag before the equilibrium sets in between the Airway tube and the self inflatable cuff so this will result in some amount of air leak.

This can be prevented if the self pressurizing cuff achieves a slightly higher pressure than the luminal pressure and at the same time it should achieve this pressure slightly before the onset of inspiration. So now the need of an hour is a device 1) which can be used to provide anaesthesia for prolonged period of maybe 6-8 hours or above
2) should provide effective sealing pressure of 40 cm of H20
3) avoid nerve injuries which were present with earlier models of Supraglottc Airway Devices (SAD)
4) which is efficient with both controlled (positive pressure) ventilation and spontaneous respiration
5) without increasing the risk of aspiration pneumonitis.

Advantages of this Invention

This invention will be having a "Dynamic cuff" which will inflate during positive pressure ventilation and it will get deflated during expiration.

Since the cuff will deflate during expiration, risk of hypoglossal or recurrent laryngeal nerve injuries due to continuous compression of the said nerves against hard structures like bones is non existent with this design.

Additionally, the "dynamic cuff" inflation will slightly precede the inflation of lung with IPPV, thereby the "sealing pressure" will be more than the "luminal pressure" at any point of time, providing a more perfect supraglottic seal.

Also, the cuff is designed in such a way that the cuff pressure will exceed the luminal pressure during all phases of the respiratory cycle thereby, providing optimal supraglottic seal during all phases of the respiratory cycle, resulting in zero air leak from the lungs during positive pressure ventilation (PPV).

The supraglottic "Dynamic cuff" will be having a specially designed "adaptor", which, when connected to a ventilator circuit/AMBU bag, will preferentially direct the air into the cuff, inflating it prior to lung inflation, and thereby providing effective seal throughout the respiratory cycle.

This device will be having a dedicated "cuff inflation lumen" along the "ventilation lumen" ("VentiLumen") of the device which will be used to inflate the cuff during positive pressure ventilation.

The "cuff inflation lumen" ("DynaLumen") will also be having a locking mechanism to enable its use like a conventional LMA; i.e., the cuff can be left continuously inflated both during positive pressure ventilation as well as less during expiratory phase and during spontaneous respiration. The dyna lumen may have a cuff inflation port with unidirectional valve by which compartment A and B can be inflated to desired pressure which can monitored by cuff manometer. This can be used during spontaneous respiration with the dynamic lumen clamped above the pilot balloon.

A small orifice may communicate between the DynaLumen and the VentiLumen allowing both the lumens to reach pressure equilibrium at the end of inspiratory phase of PPV (Positive Pressure Ventilation) so that there is no undue pressure build up in the DynaCuff.

A variant of this device will behaving a foam in the supraglottic cuff, which can be deflated at the time of the insertion of this device into the glottis and it will get expanded to its original shape and size up on exposure to atmospheric air there by snugly maintaining the contour of the cuff even when there is no positive pressure ventilation, i.e, spontaneous respiration of the patient. The foam can be included in entire compartment A and B or partially in either compartment.

The device will be having a third lumen which will go along the VentiLumen throughout the length of the shaft and will end below the supraglottic portion of the bowel enabling pharyngeal and esophageal suctioning and Ryles tube insertion.

A variation of this device will also provide a specialised ryles tube with a inflatable cuff which can be used to occlude the gastroesophageal junction and this specialised ryles tube will be provided with a guidewire so that the positioning of the ryles tube into the stomach is easy.

By having a dynamic inflation Cuff which will get inflated only during positive pressure ventilation and getting deflatted during the expiratory phase we avoid the risk of sore throat, hoarseness of voice and the risk of nerve injury of the hypoglossal and the recurrent laryngeal nerve. Along with this we also achieve satisfactory filling pressure of the supraglottic cuff by the use of especially decide adaptor and a dedicated lumen to pump air into the supraglottic cuff there by generating high sealing pressures and reducing air leak.

Because this device does not exert a continuous pressure along the pharyngeal wall the depth required for the patient to tolerate this device is much lower when compared with the conventional LMA.

This device can be used as a conventional supraglottic device if we lock the DynaLumen using the locking mechanism provided enabling the device to be used as a regular laryngeal mask Airway.

this device is provided with a dedicated esophageal port to do pharyngeal and esphageal suctioning and also to facilitate Ryles tube insertion into the stomach. The specialised GOJO tube (Gastro Oesophageal Junction Occuder tube) can be used through this port to prevent aspiration of gastric contents. Hence this device can even be used in patients with inadequate starvation or full stomach.

OBJECTS OF THE INVENTION

The main object of the invention is to give a modified supraglottic airway device (SAD) with a dynamic cuff which will provide early and better airtight Supraglottic seal enabling superior ventilating ability

DETAILED DESCRIPTION OF THE DEVICE

FIG. 1 shows device has a main body which is called a "shaft" (1). The shaft consists of three cylindrical tubes next to each other, extending all the way from the proximal end till the distal end of the shaft. The shaft is made of soft but thick silicone/any other suitable material making it washable and non kinkable.

The proximal end of the shaft is also called as the "Ventilator End" (2) and the distal end is called "Pharyngeal end" (3)

Of the three tubes, the central one is the largest. This is called the Ventilating Lumen "VentiLumen" (4) whose function is to deliver the ventilating gases in and out of the lungs via the glottis. The proximal end of the Ventilumen is connected to the special "adapter" (5) and distally it ends as the "bowl" just over the glottis, enabling Direct suctioning of the glottis bronchoscopic suction/bronchoscopy & lavage/bougie guided tracheal intubation in patients with difficult laryngoscopy and intubation.

A smaller cylindrical tube is present on one of the sides of the Ventilumen. This tube pushes the air in and out of the Dynamic Cuff during positive pressure ventilation and this lumen is called "DynaLumen" (6). The proximal end of the Dynalumen is connected to the specially designed "adapter" and its distal end in the Compartment A of the DynaCuff. Just before ending in the Compartment A of the DynaCuff, the Dynalumen also inflates the Compartment B through the side holes. (Diag No. 2)

A specially designed "adapter" (5) connects the proximal end of this device to the Ventilator circuit/AMBU resuscitator. The adapter has a proximal end (7) and a distal end has two ports (8). The proximal end has a standard 15 mm female/22 mm male port, which can be connected to the ventilator circuit/AMBU resuscitator. The distal end of the "adapter" has 2 ports: of the two, the larger one (**4*a*) is a 15 mm female port, which gets attached to the Universal connector at the proximal end of the VentiLumen. The smaller port (6*a***) is attached to the tip of the DynaLumen.

Near the proximal end of the DynaLumen lies a clip like locking system (9) which can be used to keep the Dynamic cuff continuously inflated (as may be required in spontaneous respiration) The proximal end of the DynaLumen has an adapter which enables to inflate the DynaCuff with a 3-way stopcock and a Syringe.

The third circular tube (10) is the lumen which is used to suction and removal of pharyngeal secretions and secretions this lumen also used to insert a ryles tube or a specialised GOJO tube which can be used to prevent aspiration in a patient with full stomach.

At the distal end of the shaft, the middle lumen ("Venti-Lumen") (4) ends in cavity called as "Bowl" (11). This bowl rest directly over the glottis. The ventilatory gases from here reach the lungs via the glottis. Around and behind the bowl, lies the DynamicCuff (12)

FIG. 2. Shows the back portion or the posterior aspect of the device wherein the dynamic cuff is divided into two compartments. The portion surrounding the "bowl" is the "Compartment A" (14) and the portion behind the bowl is called "Compartment B" (13). The DynaLumen extends all the way through the Compartment B into the Compartment A and ends inside the latter. En route to the Compartment A the DynaLumen inflates (and deflates) the Compartment B through its side holes(17) and its tip(18) inflates (and deflates) Compartment A. The inflation of these two compartments provide the airtight supraglottic seal during PPV (positive pressure ventilation)

A variation of this cuff design is where a deflatable sponge/foam fills partially or completely, either or both compartments of the Dynamic cuff, which can be collapsed while inserting the device into the pharynx but reexpands upon insertion to regain its original shape, thereby preventing tongue fall and airway obstruction. During PPV (positive pressure ventilation) the dynamic cuff gets inflated and provides a better seal over and above the one achieved with the SpongeCuff (DynaSponge.). Figure also shows distal end (16) of the suctioning lumen (10) and multiple apertures proximal to it for pharyngeal suctioning (15).

FIG. 3. Shows the cut section of the device at the level of the bowl wherein the portion surrounding the "bowl" is the "Compartment A" (14) and the portion behind the bowl is called "Compartment B" (13). The Dyna Lumen extends all the way through the Compartment B into the Compartment A and ends inside the latter. En route to the Compartment A the Dyna Lumen inflates (and deflates) the Compartment B through its side holes(17) and its tip(18) inflates (and deflates) Compartment A. FIG. 4 describes the special adaptor.

Figure 1:
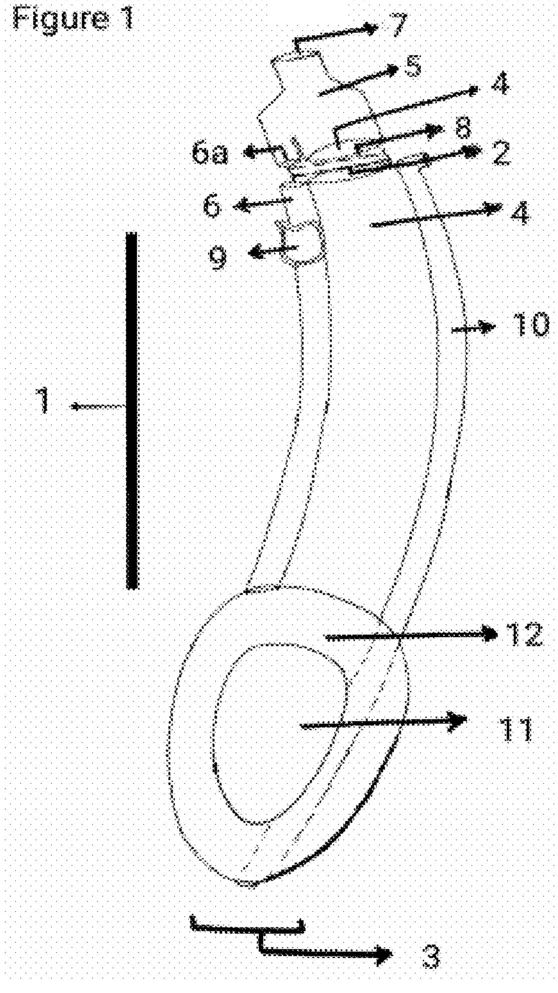
Figure 2:
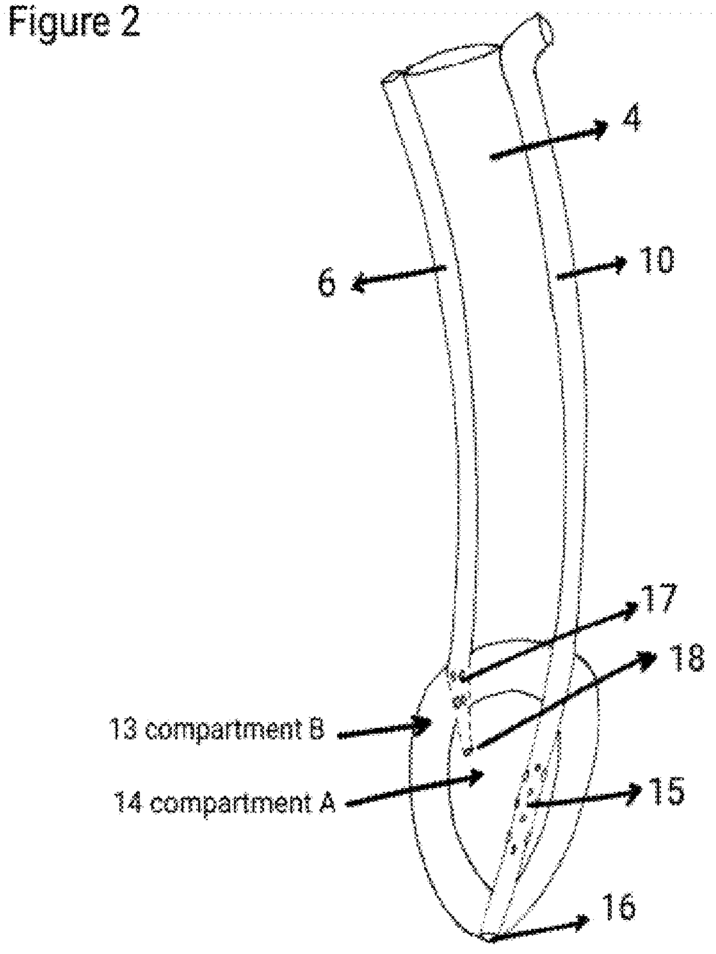
Figure 3:
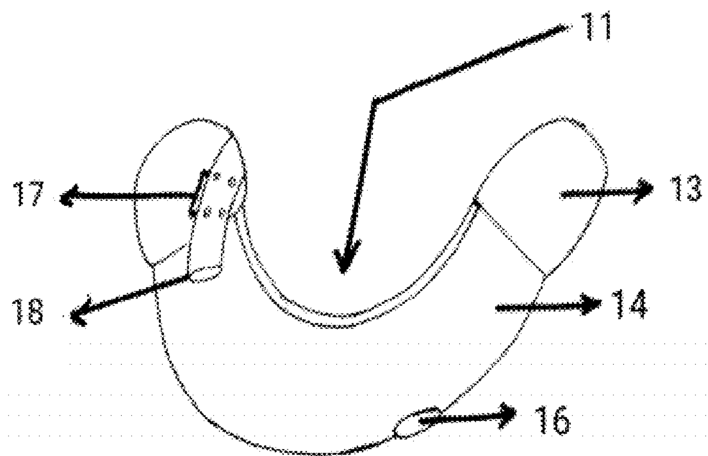
Figure 4:
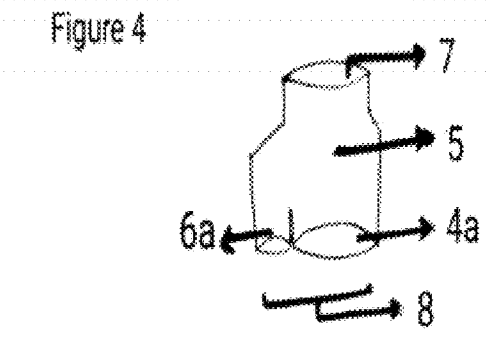
Figure 5:
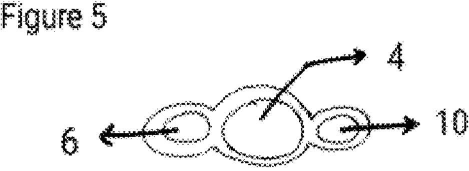
FIG. 5 shows the cut section of the Shaft. Here the central lumen(4) is the largest and it is directly connecting to the bowl(11) of the device and the two smaller lumens on the sides are the ones which inflate the DynaCuff (6) and the suction/Ryles tube insertion port (10)
Figure 6:
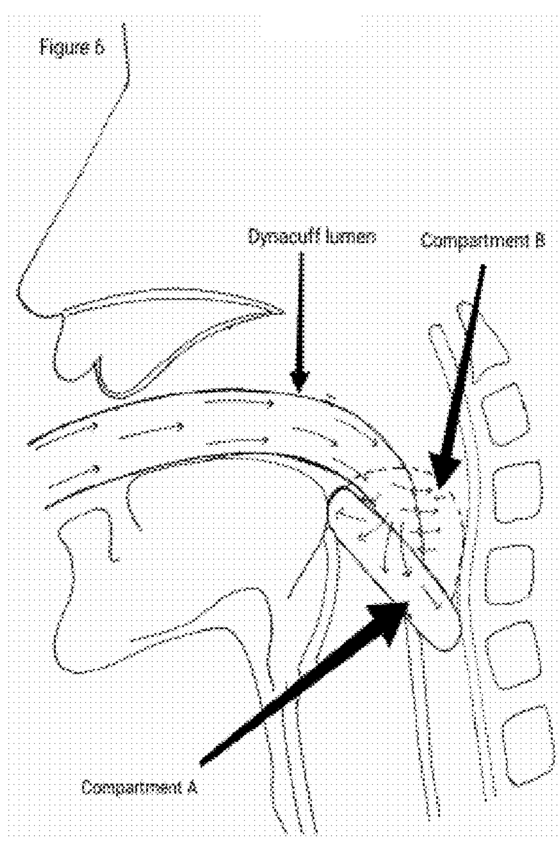
FIG. 6 shows the working model of the device in inspiratory phase within the patients pharyngeal cavity.

We claim:

1. A supraglottic airway device for insertion into an oral cavity for ventilation comprising;

a shaft comprising three cylindrical tube members: a ventilating lumen, a cuff-inflation lumen, and a suctioning lumen, each extending from a proximal end up to a distal end of the shaft arranged with their long axes parallel and adjacent to each other;

an elliptical bowl formed by a distal end of the ventilating lumen, wherein the elliptical bowl is surrounded on its sides by a dynamic cuff comprising one or two inflatable compartments on a side and at a rear of the elliptical bowl; and an adapter having a proximal end and a distal end, the distal end comprising two unequal ports, wherein the proximal end of the adapter is configured to be connected to an outlet port of a mechanical ventilator or a manual resuscitator, and the distal end of the adapter is configured to be connected through the two unequal ports to proximal ends of the ventilating lumen and the cuff-inflation lumen;

wherein the adapter diverts a portion of pressurized air from the mechanical ventilator or the manual resuscitator into the dynamic cuff in a direction essentially parallel to that of respiratory gas movement in real-time, through the cuff-inflation lumen;

wherein the one or two inflatable compartments are configured to automatically inflate during positive pressure ventilation and automatically deflate during expiration in response to the pressurized air diverted by the adapter, thereby cyclically forming and releasing an airway seal in synchronization with respiratory gas movement; and wherein the suctioning lumen is provided with apertures proximal to a distal end of the suctioning lumen and allows pharyngeal suctioning through these apertures, thereby improving the airway seal.

2. The supraglottic airway device of claim 1, wherein the cuff-inflation lumen extends from the proximal end of the shaft, along the ventilating lumen up to the distal end of the shaft, and terminates inside the one or two inflatable compartments.

3. The supraglottic airway device of claim 1, wherein the ventilating lumen extends from the proximal end of the shaft up to the distal end of the shaft, where it terminates forming the elliptical bowl that rests over a glottis upon appropriate positioning inside an oral cavity, when in use.

4. The supraglottic airway device of claim 1, wherein the suctioning lumen extends from the proximal end of the shaft along the ventilating lumen and extends behind the elliptical bowl up to the distal end of the shaft, to open up into an oesophageal lumen of a patient, when in use.

5. The supraglottic airway device of claim 1, wherein the proximal end of the adapter has a standard port that fits into the mechanical ventilator or the manual resuscitator.

6. The supraglottic airway device of claim 1, wherein the two ports of the distal end of the adapter are two unequal terminals wherein a larger terminal is connected to the proximal end of the ventilating lumen and a smaller terminal is connected to the proximal end of the cuff-inflation lumen.

7. The supraglottic airway device of claim 1, wherein the one or two inflatable compartments, are configured to inflate with the ventilation of the cuff-inflation lumen directly, or through interconnecting holes on a wall of the cuff-inflation lumen.

8. The supraglottic airway device of claim 1, wherein the dynamic cuff contains a compressible sponge or foam that fills at least one of the one or two inflatable compartments of the dynamic cuff, which allows to be collapsed while inserting the device into the pharynx but re-expands upon insertion to regain its original shape upon exposure to atmospheric pressure.

9. The supraglottic airway device of claim 1, wherein one of the one or two inflatable compartments is kept inflated permanently and the other compartment alone is self-pressurized with positive pressure ventilation.

* * * * *